United States Patent [19]
Shen et al.

[11] Patent Number: 5,872,860
[45] Date of Patent: Feb. 16, 1999

[54] CALIBRATION CASSETTE FOR USE IN CALIBRATING AN AUTOMATED AGGLUTINATION REACTION ANALYZING SYSTEM

[75] Inventors: Jian Shen, Princeton, N.J.; Thierry Dupinet, Zurich, Switzerland

[73] Assignee: Ortho Diagnostic Systems, Inc., Raritan, N.J.

[21] Appl. No.: 816,314

[22] Filed: Mar. 13, 1997

[51] Int. Cl.[6] .............................. G06K 9/00; G01N 33/48
[52] U.S. Cl. ............................................. 382/128; 356/42
[58] Field of Search .................................. 382/128, 129, 382/133, 134; 356/42, 243; 702/19; 436/8; 422/73

[56] References Cited

U.S. PATENT DOCUMENTS

| | | | |
|---|---|---|---|
| 4,055,376 | 10/1977 | Daberko | 350/10 |
| 4,557,599 | 12/1985 | Zimring | 356/243 |
| 4,727,033 | 2/1988 | Hijikata et al. | 436/69 |
| 5,132,097 | 7/1992 | Van Deusen et al. | 422/82.09 |
| 5,338,689 | 8/1994 | Yves et al. | 436/518 |
| 5,485,527 | 1/1996 | Bacus et al. | 382/128 |

*Primary Examiner*—Andrew W. Johns
*Attorney, Agent, or Firm*—Dana M. Schmidt

[57] ABSTRACT

A method, and a calibration device, for calibrating a system for analyzing aqueous solutions and that includes a pixel array and a variable focus line for focusing onto the pixel array illuminated images of the aqueous solutions. The method includes the steps of illuminating a pattern on the calibration device to form an illuminated image of that pattern, and directing that illuminated image through the lens and onto the pixel array. The method includes the further step of deriving data values representing the image on the pixel array, and using those data values to adjust the focus of the lens and to adjust the position of the calibration device relative to the pixel array.

3 Claims, 8 Drawing Sheets

CALIBRATION CASSETTE FOR USE IN CALIBRATING AN AUTOMATED AGGLUTINATION REACTION ANALYZING SYSTEM

BACKGROUND OF THE INVENTION

This invention generally relates to systems that use automated image processing techniques to detect and quantify agglutinates formed in response to immunological agglutination reactions. More particularly, the present invention relates to methods and apparatus for calibrating such systems.

Immunological agglutination reactions are used to identify blood types and to detect antibodies and antigens in blood samples and other aqueous solutions. In a conventional procedure, a sample of red blood cells is mixed with serum or plasma in test tubes or micro plates, and the mixture is then centrifuged. Commonly, but not necessarily, the mixture is also incubated before being centrifuged. Various reactions either occur or do not occur in the mixture depending on, for example, the blood type of the red blood cells, or whether certain antibodies are present in the blood sample.

Typically, these reactions manifest themselves as clumps of cells or particles, referred to as agglutinates, having antigens and antibodies on their surfaces. The absence of any such clumps thus indicates that no reaction has occurred, and the presence of such Clumps indicates that a reaction has occurred. In addition, if a reaction has occurred, then the size and amount of the formed clumps are quantitative indicators of the level or concentration in the sample of the complex for which the blood sample was tested. The size and amount of the formed clumps are also quantitative indicators of the affinity of that complex for the reagent used to produce the reaction.

Recently, a new agglutination test method—referred to as column agglutination technology, or CAT—has been developed. Column agglutination technology may be defined as the analysis of blood and blood products utilizing filtration as a means of separating agglutinated, precipitated, absorbed, or adsorbed particulate components from non reactive components for immunoassay applications. In this method, gel or glass bead micro particles are contained within a small column, referred to as a microcolumn. A reagent such as anti-IgG is dispensed in a diluent in the microcolumn and a test red blood sample is placed in a reaction chamber above the column. The column, which is typically one of a multitude of columns formed in a transparent cassette, is then centrifuged.

The centrifuging accelerates the reaction, if any, between the reagent and the blood sample and also urges the cells of the blood sample toward the bottom of the column. The glass beads or gel in the microcolumn act as a filter, however, and resist or impede downward movement of the particles in the column. As a result, the nature and distribution of the particles in the microcolumn after centrifuging provide a visual indication of whether any agglutination reaction occurred in the microcolumn, and if so, of the strength of that reaction.

In particular, if no agglutination reaction occurs, then all or virtually all of the cells of the blood sample in the microcolumn pass downward during centrifuging to the bottom of the column, and these cells form a pellet at that bottom. In contrast, if there is a very strong reaction between the reagent and the blood sample, virtually all of the cells of the sample agglutinate, and large agglutinates form at the top of the microcolumn, above the gel or glass beads contained therein. The gel or glass beads prevent the agglutinates from passing to the bottom of the column during centrifuging, so that after centrifuging, the agglutinates remain above the gel or beads.

If there is a reaction between the reagent and the blood sample, but this reaction is not as strong as the above-described very strong reaction, then some but not all of the cells of the blood sample agglutinate. The percentage of the cells that agglutinate and the size of the agglutinated particles both vary directly with the strength of the reaction. During centrifuging, the unreacted cells pass to the bottom of the column, and the distance that the agglutinated particles pass downward through the column depends on tile size and number of the particles. Hence, the size of the pellet of cells at the bottom of the microcolumn, and the extent to which the agglutinates penetrate into the gel or glass beads in the microcolumn, are both inversely related to the strength of the reaction between the reagent and the blood sample.

Conventionally, an agglutination reaction pattern is classified as either negative or positive, and if positive, the reaction is then further classified into one of a series of classes depending on the strength of the reaction. Traditionally, the classification is done by a human technician or operator who observes, or reads, the reaction pattern in the column. The use of human technicians for this purpose has several disadvantages. For example, the technicians need to be highly skilled and trained to read and to classify the reactions properly. Also, even with highly skilled and trained technicians, the classifications are subject to human interpretation, and as a result, it is believed that the consistency and reproducibility of the classifications can be improved. Because of these disadvantages, efforts have been made to automate the classification of the agglutination reactions.

One automated system for reading and classifying agglutination reactions in microcolumns is disclosed in copending application Ser. No. 08,/163,996 for "Method and System For Classifying Agglutination Reactions." The method disclosed in this copending application is based on a computerized imaging system. In accordance with this method, an image of an agglutination reaction is formed on an array of pixels, and those pixels generate electric charges that are converted to digital data values. These data values are then processed according to a predetermined program to determine if an agglutination pattern is present in the image, and, if so, to classify that pattern into one of a plurality of predefined classes. In order to obtain consistent test results with this system, it is desirable to calibrate the system regularly.

SUMMARY OF THE INVENTION

An object of the invention is to calibrate an imaging system used for analyzing solutions for agglutination patterns.

Another object of the present invention is to provide a procedure for adjusting solution imaging systems to generate the images with consistent intensity and contrast and for verifying the performance of the system hardware and software.

A further object of this invention is to provide a calibration cassette, which is used for analyzing solutions for agglutination patterns, with a photographic gray scale to determine and adjust the dynamic range of the imaging system, and with printed images of agglutination reactions to verify the system and the system software.

These and other objectives are obtained with a method for calibrating a system for analyzing aqueous solutions and that includes a pixel array and a variable focus lens for focusing illuminated images of the aqueous solutions onto the pixel array. The method includes the steps of providing a calibration device having a pattern thereon, illuminating that pattern to form an illuminated image thereof, and directing that illuminating image through the lens and onto the pixel array. The method includes the further steps of deriving data values representing the image on the pixel array, and using those data values to adjust the focus of the lens and to adjust the position of the calibration device relative to the pixel array.

Preferably, the calibrating device includes printed images of different agglutination reactions and a photographic gray scale including a plurality of strips having different optical densities. The gray scale may be used to determine and adjust the dynamic range of the imaging system. The agglutination reaction images may be used to determine scan positions for the test cassettes and to verify the imaging equipment and the software of the image analysis system. The procedure and the calibration device of this invention can also be used in the regular quality control of the imaging system and to monitor the long term stability of the system.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENTS

Figure 1:
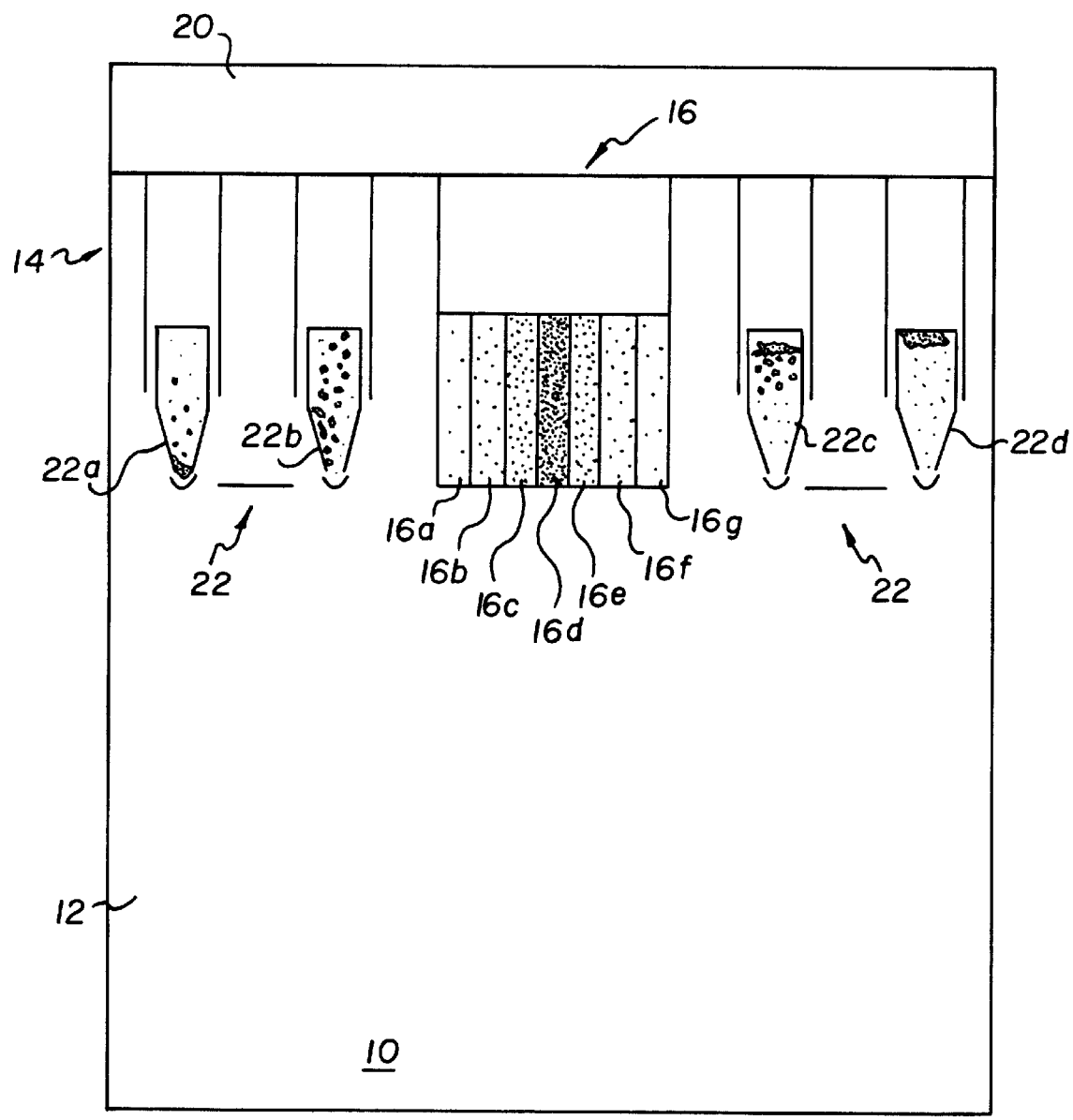
FIG. 1 illustrates a calibration cassette that may be used to calibrate an automated agglutination reaction analysis system.

FIG. 1 shows calibration cassette 10 comprising base or body 12 and an image pattern 14 formed thereon. Preferably, cassette 10 is manufactured by printing pattern 14 on a transparent material such as glass. With the preferred embodiment of cassette 10 shown in FIG. 1, the image pattern 14 includes a photographic gray scale 16 that, in turn, includes multiple strips 16a, 16b, 16c, 16d, 16e, 16f and 16g having different optical densities, an opaque white area 20 that reflects incident light and blocks transmitting light, and an area 22 including pictures 22a, 22b, 22c and 22d of four agglutination reactions typically seen in a microcolumn. A holder (not shown) may be fixed to the top side of cassette 10 and used to help move the cassette. In particular, this holder may be used to connect the cassette to, or to mount the cassette on, an automated mover that, in turn, is used to move the cassette.

In the calibration process, described in greater detail below, an illuminated image of the calibration cassette is produced on an array of pixels. These pixels generate electric charges representing the light intensity pattern of the illuminated image on the pixel array, and these electric charges are converted to digital data values. These data values are then processed according to a predetermined program; and on the basis of information found in the image, the program will either automatically adjust the system or signal the operator to request a manual adjustment.

The photographic gray scale 16 is used to adjust the gain and offset values of an imaging board, discussed in greater detail below, in order to obtain consistent intensity and contrast in the images. More specifically, as mentioned above, the photographic scale 16 includes multiple strips 16a–16g of different optical density values. The optical density (OD) of a strip is defined as: OD=log $(I_i/I_t)$, where $I_i$ is the intensity of incident light and $I_t$ is the intensity of transmitted light. Thus, a high optical density value corresponds to a low percentage of light transmission, and a low optical density value corresponds to a high percentage of light transmission.

The values chosen for the optical densities of strips 16a–16g may be selected on the basis of the desired dynamic range for the data values representing the intensity of the image on the pixel array. In an imaging system used for blood analysis, the pixels in the image of the red blood cells may be given low values, and the pixels in the brightest area of the cassette image may be given high values. For instance, if the pixels are assigned data values between 0–255, the pixels in the image of the red blood cells may be assigned a value of 10, and the pixels in the brightest area of the cassette image may be assigned a value of 245. This intensity range provides an excellent contrast without the saturation of that image intensity.

To adjust the gain and offset of the imaging board, a minimum of two strips with two different optical densities are required. However, in order to test the linearity of the light conditions, more strips of different optical densities are preferably used. For example, in an embodiment that has been actually reduced to practice, gray scale 16 includes seven strips 16a–16g having four different optical density levels: 2.5, 0.44, 0.19 and 0.09.

Strips 16a–16g may be arranged on the calibration cassette 10 in a variety of specific patterns. In a preferred embodiment, these strips are parallel to each other and form a row. The strip with the highest optical density is placed in the middle of that row, and the other strips are positioned about that strip with the optical densities of the strips decreasing in the direction extending away from that middle strip and with corresponding strips; on the left and right sides of that middle strip having equal optical densities. In particular, the two strips 16c and 16e having the second highest optical density are located immediately to the left and right of the middle strip 16d, the two strips 16b and 16f having the third highest optical density are located immediately outside of strips 16c and 16e, and the two strips 16a and 16g having the lowest optical density are located on the left and right ends of the row of strips. This arrangement of strips is useful to test the symmetry of the light conditions in the imaging system.

Above the photographic scale 16 is the opaque white area 20. As mentioned above, this opaque area reflects the light incident from the side of cassette on which the pixel array is located, but blocks the transmission of light from the opposite side. As discussed in greater detail below, by measuring the gray value of the image on the pixel array of this opaque region, the intensity of light from the pixel side of the cassette can be determined.

The calibration cassette also has four printed pictures 22a–22d of agglutination reactions. These pictures represent typical reactions that can be observed in the blood analysis with a CAT method. As discussed below, these pictures are used to verify the system and image processing software after the above-discussed adjustments are made.

Figure 2:
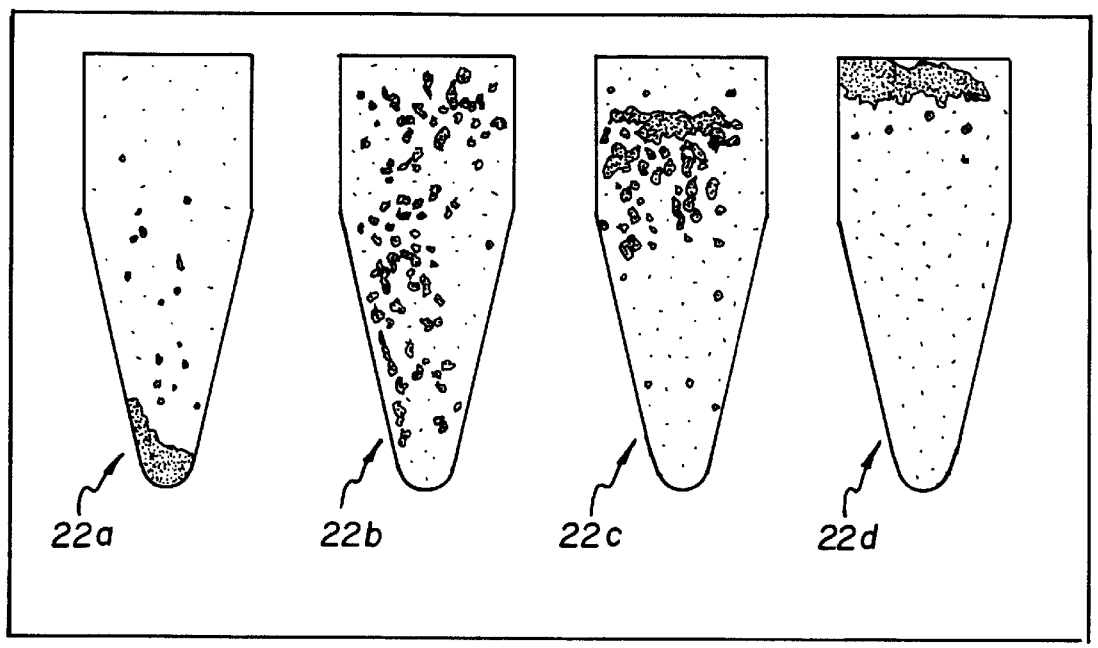
FIG. 2 shows different agglutination patterns on the calibration cassette.

FIG. 2 shows image prints 22a–22d in greater detail. Reaction picture 22a represents a weak positive reaction that is normally classified as a +0.5 reaction. In this type of weak reaction, some of the cells in the blood sample agglutinate and form a few, small agglutinate particles; however, most of the sample cells do not react. During centrifuging, agglutinated particles become distribute in the lower half of the microcolumn, and the unreacted cells of the sample pass to the bottom of the column and form a pellet.

Reaction picture 22b represents a typical +2 reaction. In this reaction, a significant percentage of cells in the blood sample react and agglutinate. During centrifuging, the unreacted red pass through the column and form a small pellet in the bottom of the microcolumn, and agglutinated particles become distributed throughout the length of the column.

Reaction picture 22c shows a class +3 reaction in which most of the cells in the blood sample agglutinate and the agglutinated particles remain in the upper half of the microcolumn after centrifugation. In a class +4 reaction, as shown in reaction picture 22d, all, or virtually all, of the cells in the blood sample agglutinate and form large agglutinates at the top of the filter in the microcolumn.

Figure 3:
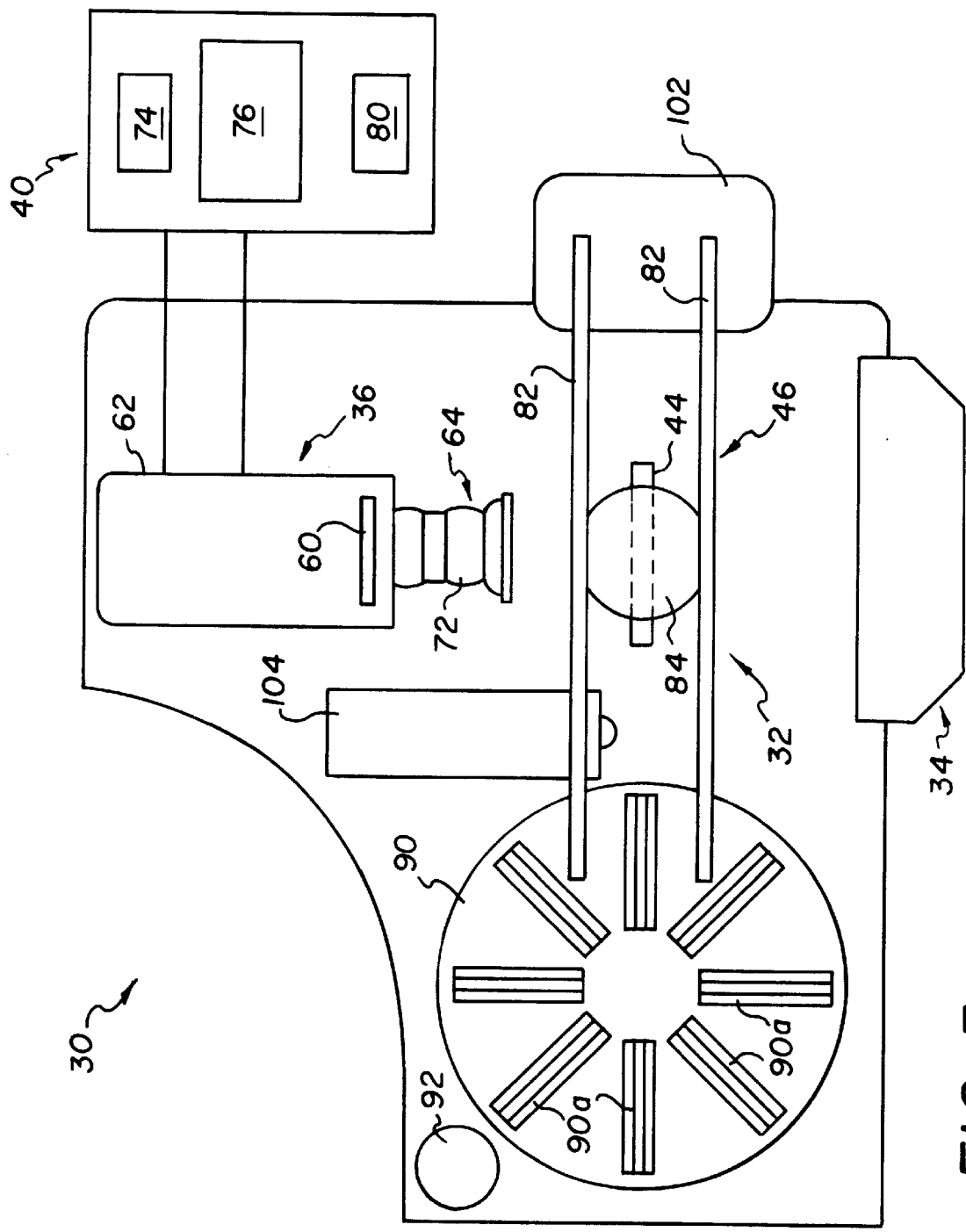
FIG. 3 is a schematic diagram of an automated agglutination reaction analysis system.
Figure 4:
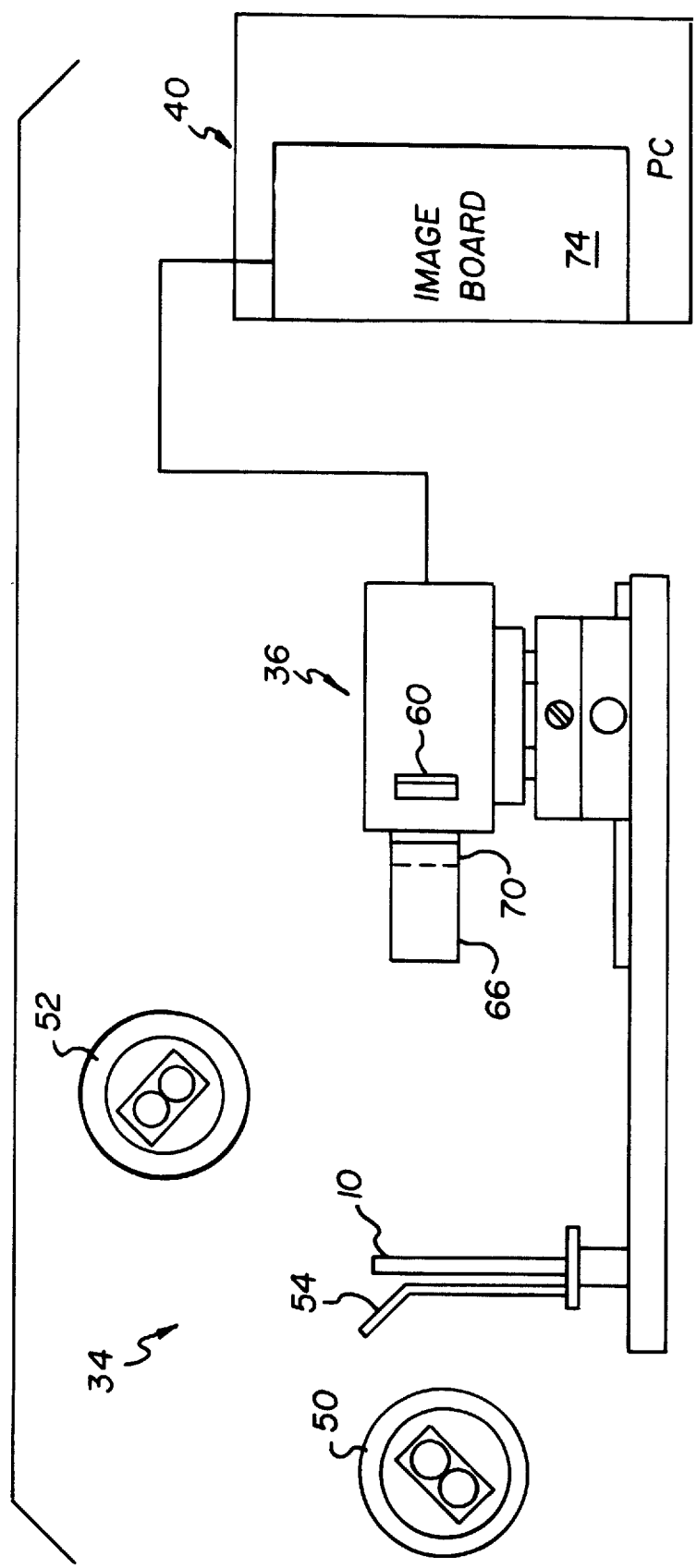
FIG. 4 is a block diagram illustrating several components of the system of FIG. 3.

FIGS. 3 and 4 illustrate an image processing system 30 for analyzing and classifying agglutination reactions and that may be calibrated using cassette 10. System 30 is similar to the automated analysis system discussed in detail in copending application Ser. Nos. 08/163,996 and 08/075,028, the disclosure of which are herein incorporated by reference.

Generally, system 30 includes cassette positioning subsystem 32, illumination subsystem 34, imaging subsystem 36, and data processing subsystem 40, and preferably system 30 further includes storage subsystem 42. With the embodiment of system 30 shown in FIGS. 3 and 4, the cassette positioning subsystem includes cassette holder 44 and transport assembly 46, and the illumination subsystem includes a pair of fluorescence lights 50 and 52 and diffuser 54. The imaging subsystem includes pixel array 60, housing 62 and lens assembly 64; and this lens assembly 64, in turn, includes lens 66, filter 70 and lens housing 72. In addition, the preferred data processing subsystem 40 includes preprocessor 74, main processor 76 and input means such as keyboard 80.

Generally, positioning subsystem 32 is provided to position and to hold a cassette while an image of the cassette is formed on imaging subsystem 36, and illumination subsystem 34 is provided to produce that illuminated image of the cassette on the imaging subsystem. When this image is produced on the imaging subsystem, this subsystem generates a set of signals representing the illuminated image formed thereon. These signals are transmitted to data processing subsystem 40, and this subsystem receives those signals and processes those signals according to a predetermined program. Storage subsystem 42 may be provided to store cassette 10.

More specifically, storage subsystem 42 includes rotatable carousel 90 and an indexing means, such as a stepper motor, schematically referenced at 92. Carousel 90 is located adjacent positioning subsystem 32, and the carousel forms a multitude of compartments or slots 90a for holding cassette 10 and the test cassettes. Stepper motor 92 is used to rotate carousel 90 through a series of positions to align the cassettes therein with holder 44 of positioning subsystem 32.

Transport assembly 46 of positioning subsystem 32 includes a pair of rails 82 and a motor 84. Left ends of the rails 82 are located above carousel 92, and the rails extend horizontally therefrom, to the right as viewed in FIG. 3. Motor 84 is supported by rails 82 for sliding movement therealong. Holder 44 is provided to grip and to hold releasably the cassettes, and the holder is connected to and is supported by motor 84 for sliding movement therewith along rails 82. Motor 84 may also be used to rotate holder 44, and any cassette held by the holder, about a vertical axis.

In use, motor 84 and holder 44 are slid to a position over carousel 90, and the carousel is rotated to align a cassette with the holder. Holder 44 then grips the cassette, and the holder and motor 84 are slid to the right as viewed in FIG. 3 to move that cassette into a position directly forward of pixel array 60. After the desired imaging of the cassette is completed, holder 44 and motor 84 are moved further along rails 82 to move the cassette out of the imaging position. The cassette may be deposited in a waste receptacle 102 or the cassette may be moved to another location where the cassette may be stored for later use. A bar code reader 104 may be provided to help identify the cassettes as they are moved in system 30, and in particular, as those cassettes are moved from carousel 90 to frame 84.

Illumination subsystem 34, which preferably comprises a pair of fluorescence lamps 50 and 52, directs light through the cassette in frame 84 and onto imaging subsystem 36, and specifically onto pixel array 60, which then generates a series of signals representing the illuminated image formed on the pixel array. More specifically, pixel array 60 is disposed inside a camera housing 62, and the pixel array is comprised of a multitude of light sensors, each of which is capable of generating a respective one electric current having a magnitude proportional to or representing the intensity of light incident on that sensor. These light sensors, or pixels, are arranged in a uniform grid of a given number of uniformly spaced rows and columns.

Lens 66 and filter 70 are located forward of pixel array 60 and are coaxially aligned with each other and with the pixel array, and lens 66 is positioned so that the pixel array is at the back focal plane of this lens. Preferably, lens 66 and filter 70 are mounted inside housing 72, which is mounted on the front end of camera 62.

Figure 5:
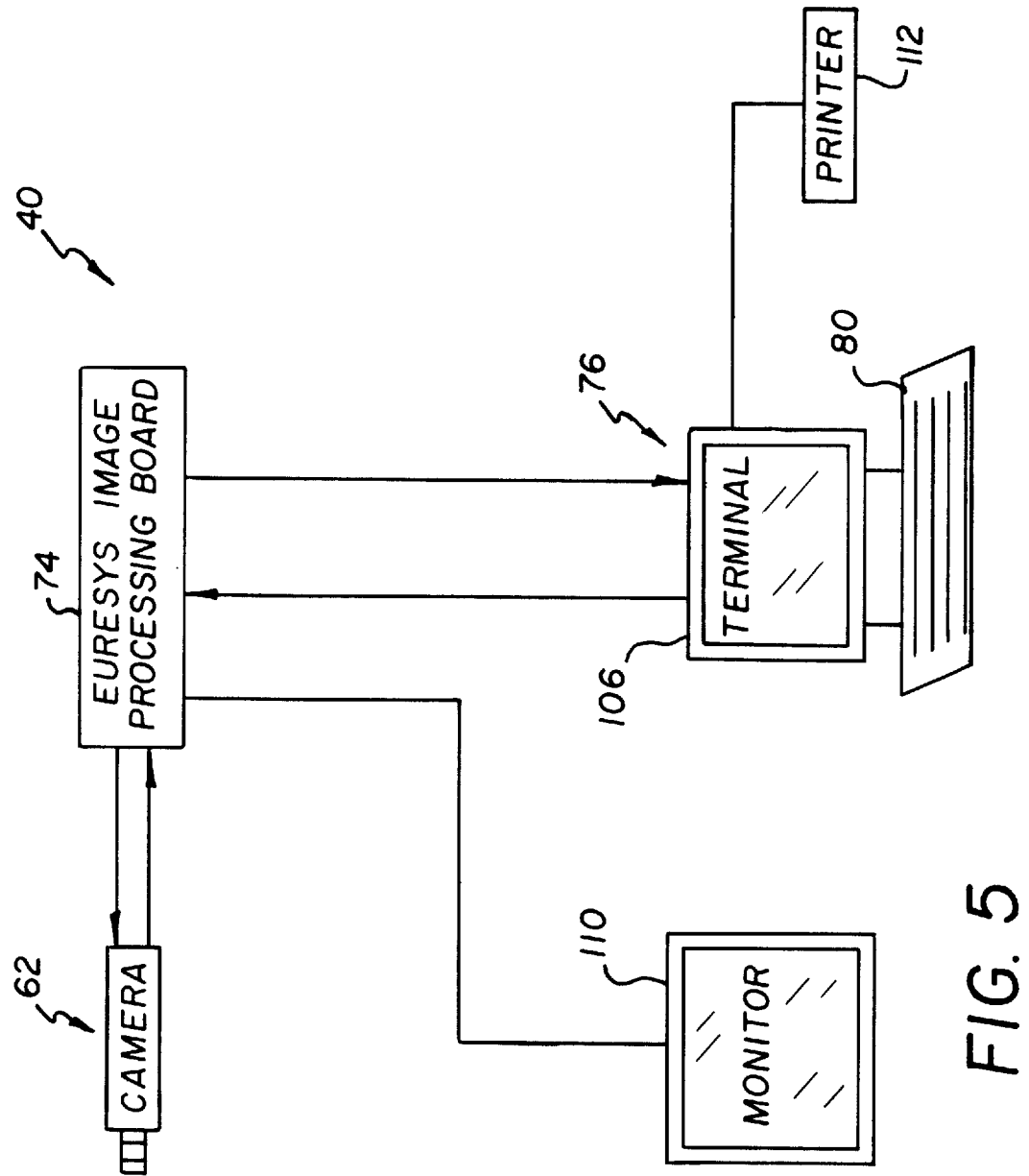
FIG. 5 is a block diagram illustrating in greater detail a processing subsystem of the analysis system of FIG. 3.

FIG. 5 is a block diagram illustrating processing subsystem 40 in greater detail. In this subsystem, the electric signals from the pixel array in camera 62 are conducted to preprocessor 74, which may be, for example, an image processing board made by Eureysys SA of Begium. This image processor 74 then converts the electric signal from each pixel of array 60 into a respective one digital data value and stores that data value in a memory location having an address associated with the address of the pixel that generated the electric signal. The electric signals being transmitted to the image processor 74 may be identified in any suitable way with the specific pixel that generated the signal.

The data values stored in image processor 74 are available to main processor 76, which is connected to the image processor to obtain data values from and to transmit data values to that image processor. As explained in greater detail below, processor 76 is programed to process and to analyze data values stored in the image processor 74.

Preferably, main processor 76 is, or is a component of, a personal computer also having keyboard 80 and terminal 106. Keyboard 80 is connected to processor 76 to allow operator input thereto, and terminal 106 is used to display visually data or messages being input into the processor. In addition, monitor 110 may be connected to processor 76 to produce video images from the data values stored in the data processor 76 or in image processor 74. Printer 112 may be connected to processor 76 to provide a visual, permanent record of selected data values transmitted to the printer from the processor.

As will be understood by those of ordinary skill in the art, system 30 and the components thereof may be provided with other or additional devices not specifically described herein. Also, it should be noted that system 30 is only an example of a system in which calibration cassette 10 can be used, and this cassette may be used in other systems.

Figure 6A:
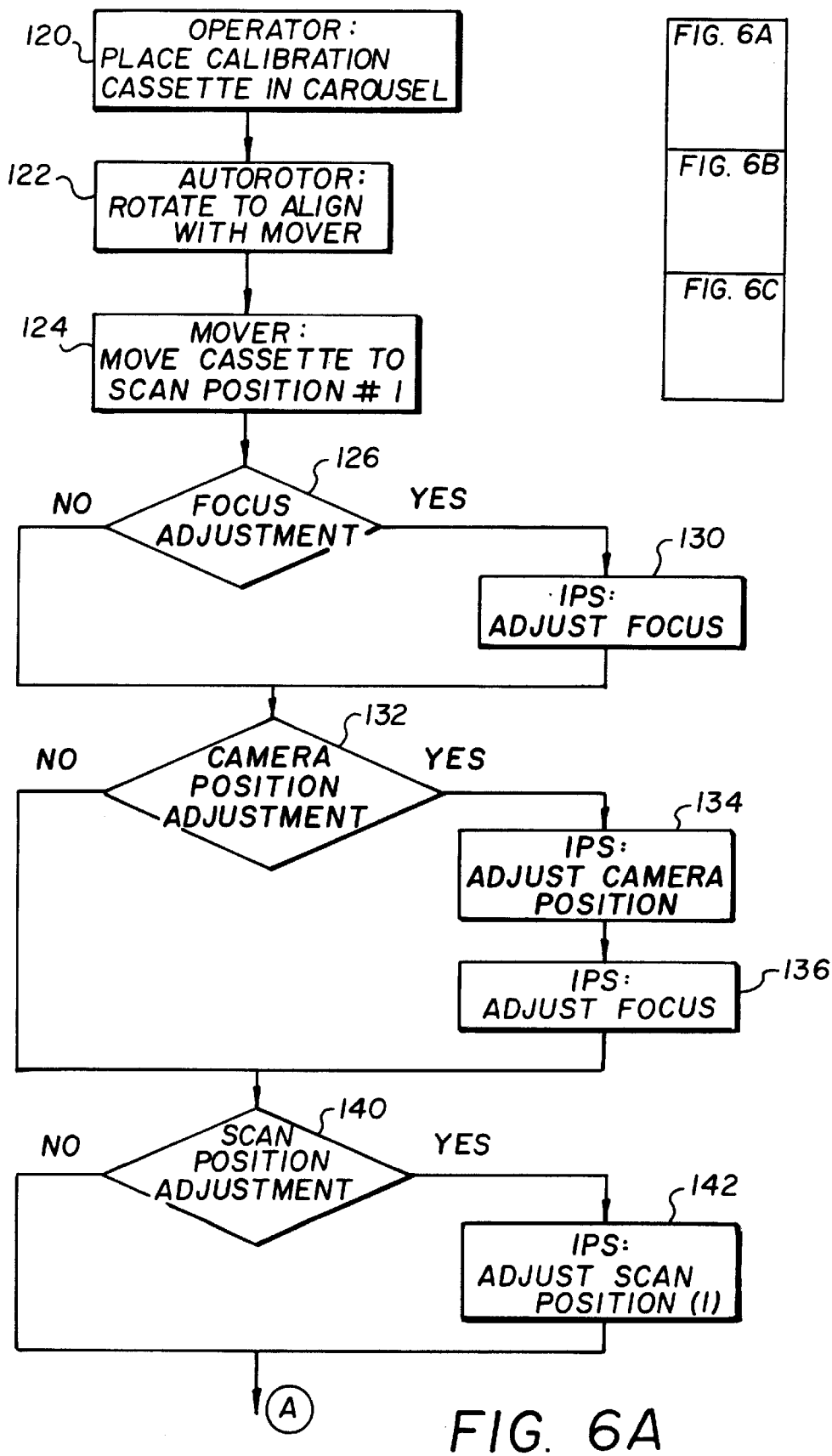
FIGS. 6A, 6B and 6C are flow charts showing a procedure for using the cassette of FIG. 1 to calibrate the analysis system of FIGS. 3 and 4.
Figure 6B:
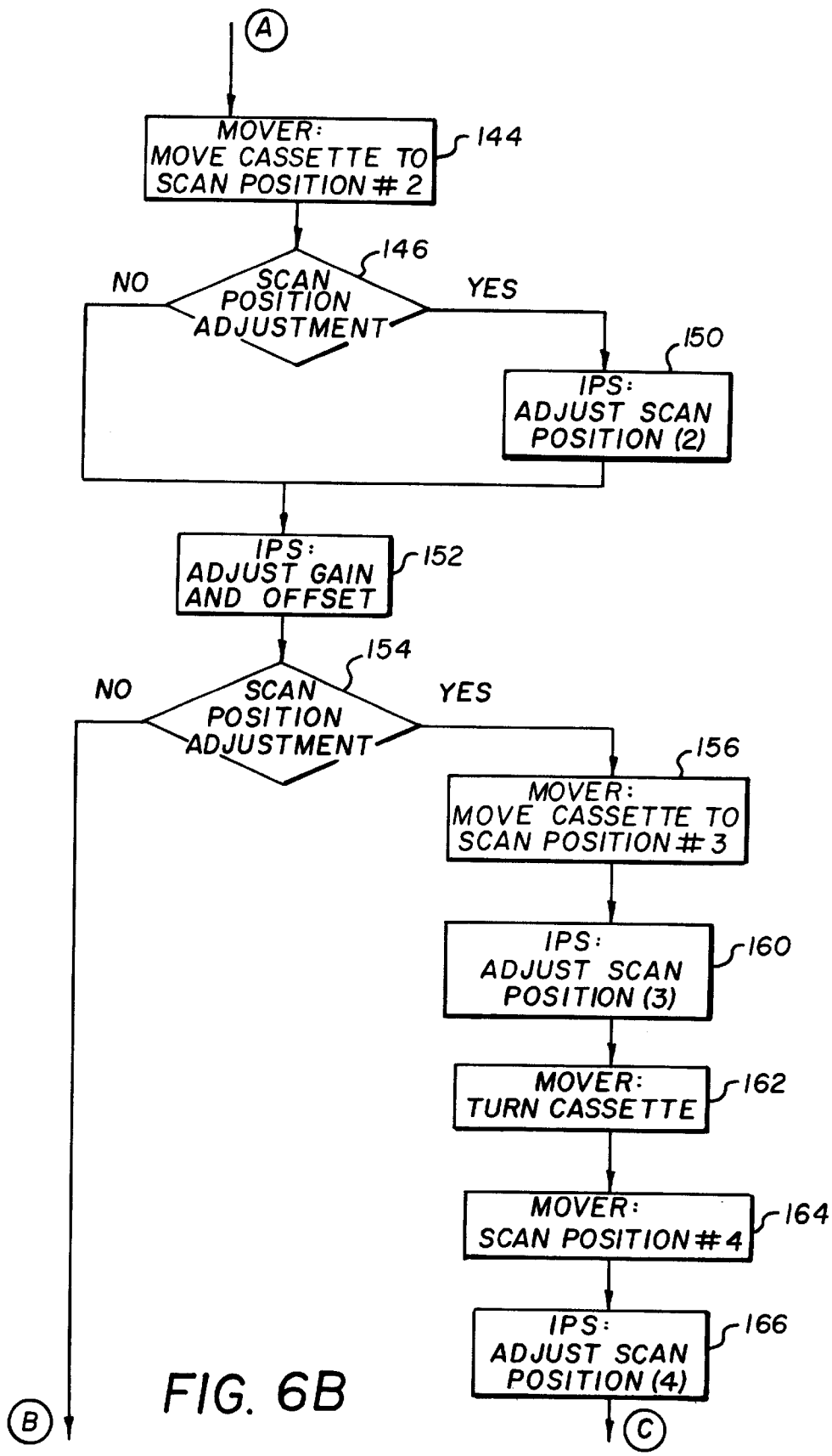
Figure 6C:
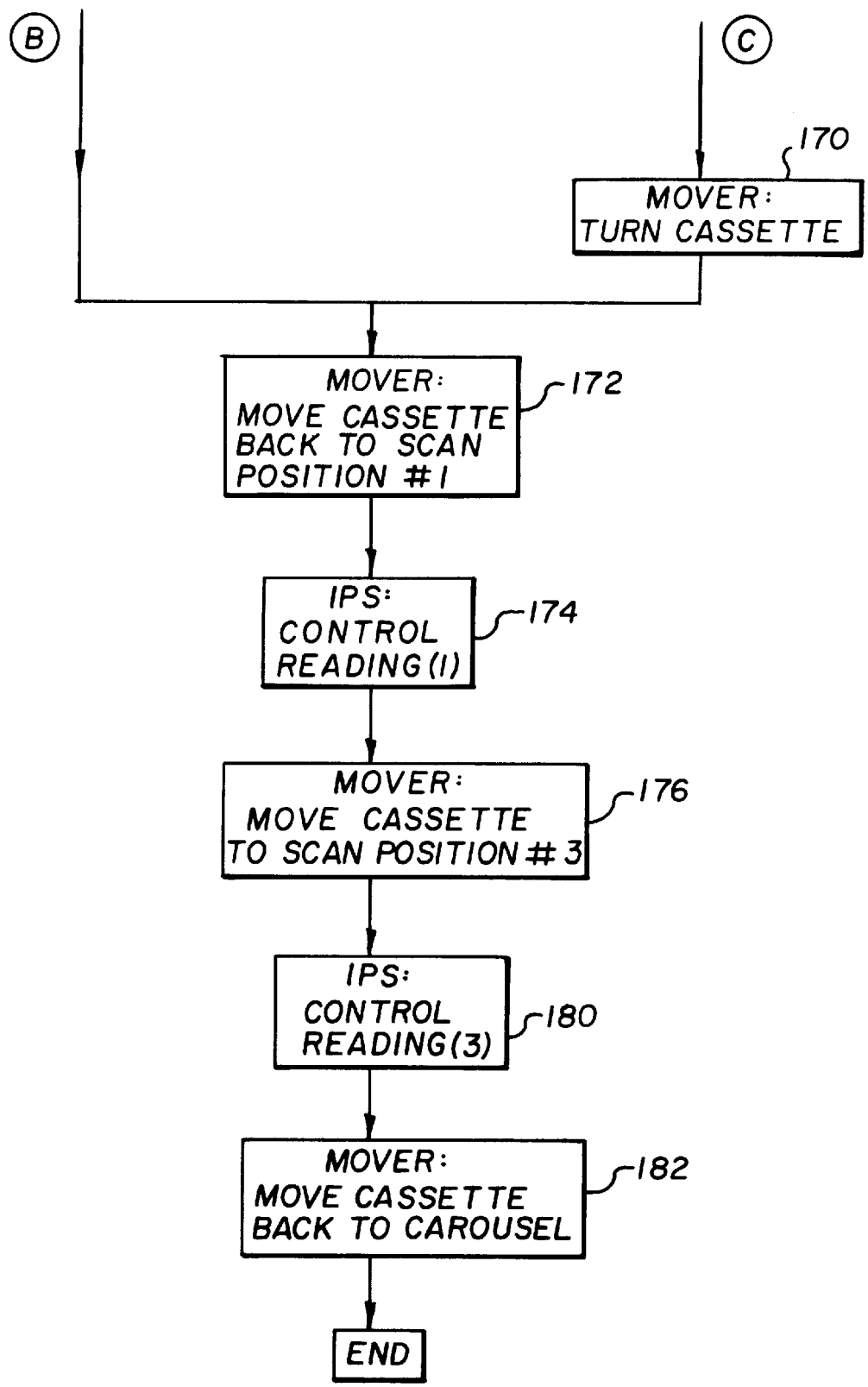

The present invention relates to calibrating system 30, and a preferred procedure for doing this shown in FIGS. 6A, 6B and 6C. In this preferred calibration process, and as represented by steps 120, 122 and 124 of FIG. 6A, calibration cassette 10 placed in a slot 90*a* in the carousel, and the carousel is rotated to align the slot into the position of the mover 94. The mover 94 then grips the cassette 10, and moves the cassette to, and holds the cassette in, a position in front of the pixel array 60. The illumination subsystem 34 directs a beam of light through the cassette 10 and onto the pixel array 60. The image acquisition program sends a synchronization signal to the camera 62 to produce an image of the cassette on the pixel array 60, and the image is then grabbed by the image processing board 74 and converted into digitized signals.

Depending on the required image resolution and the number of columns in a cassette, one or more images may be taken for a single cassette. For example, when system 30 is used to analyze test cassettes, three images may be taken of each side of a cassette that has six microcolumns; and therefore a total of six images may be taken for a single cassette with each image having two columns. Accordingly, for the calibration cassette 10, a first image taken at a first scan position contains the reaction pictures 22*a* and 22*b*, a second image corresponds to the gray scale 16, and a third image is for the reaction pictures 22*c* and 22*d*.

After the imaging board 74 successfully obtains the image of the calibration cassette 10, the software program starts to process the image data and to adjust the image processing system. As represented by steps 126 and 130 of FIG. 6A, if a focus adjustment option is selected by the operator, then the calibration program measures the focus of the camera lens 66 using the agglutinate pattern printed on the calibration cassette 10. If the camera lens 66 is on focus, the image of the agglutinates on the pixel array has sharp edges. This results in high values for the derivative of the image intensity data values obtained from the pixels in those image edges. In contrast, if the camera is out of focus, the edges of the image of the agglutinates on the pixel array are blurred, and the derivative values of the image intensity values obtained from the pixels in those image edges are decreased.

In the preferred adjustment process, the program continuously calculates the sums of the derivative values for the images of a pair of the reaction pictures 22*a*–22*d* and shows those sums on a computer monitor at short time intervals while the operator is slowly rotating the lens 66. When the derivative value reaches a maximum, or reaches a desired range, the optimal focus is reached and the adjustment can be stopped.

After completing the focus adjustment, the program begins to measure the image resolution, as represented by steps 132 and 134. This resolution is dependent on the distance between the camera 62 and the cassette 10 under a defined lens 66, and the image resolution can be calculated from the distance between two vertical lines, such as two column borders in the image. To measure this distance, the program first searches for the positions of the two borders using an edge detection program, and a variety of edge detection methods may be used for this purpose.

In a preferred embodiment, the edge detection program is based on a derivative method. In this method, the program first generates two windows on the left and right sides of the image frame to cover the two column borders. Then, the gray values in each window are projected into a one dimensional vector. At each point on each vector, a projected value is obtained by adding the gray values of all the pixels in the vertical line through that point. The derivatives of these sums of the gray values are determined and the maximum derivative values are obtained. These maximal derivative values correspond to the maximal variation of the gray scale and therefore determine the locations of the two borders.

Once the locations of the two column borders are found, the distance between these two borders can be calculated. If this distance is not in a predefined range, the program indicates that the camera position needs to be adjusted. If the distance between the two column borders is smaller than a pre-defined lower value, then the camera 62 needs to be moved closer to the cassette 10 to increase the image resolution. If the distance between the two column borders is more than a pre-defined upper value, then the camera 62 should be moved away from the cassette 10 to decrease the image resolution. Preferably, in this adjustment process, the program continuously determines the distance between the two column borders and shows these distance values on the computer monitor. A human operator can read these values and slowly move the camera toward or away from the cassette until the desired distance value is reached.

Because the focus of the cassette image on the pixel array 60 is dependent on the distance between the camera 62 and the pixel array, the focus of the camera lens 66 needs to be re-adjusted after the camera is located the preferred distance from the pixel array, as represented by step 136 in FIG. 6A, and preferably the above-described procedure for focusing the cassette image is repeated to re-focus that image. After the readjustment of this focus, the calibration program begins to adjust the different scan positions at which the mover 94 holds the cassette to generate the cassette image on the pixel array, as represented by step 140. This adjustment is based on the symmetrical location of the columns in the image frame, and these columns are located by using any suitable edge detection method.

For instance, an edge detection procedure similar to the one described above may be used to locate these columns. Preferably, the adjustment of these scan positions are performed automatically by the data processing system sending commands to a stepper motor that controls the mover 94. These commands operate the stepper motor to move the calibration cassette 10 so that the columns of interest are symmetrically located relative to the center of the image frame. After this adjustment is completed, the position of the cassette 10 is recorded, and this position is used as a reference to locate the test cassettes during analysis of the blood samples therein.

After finishing a first scan position adjustment as represented by step 142, the calibration cassette, at step 144, may be moved to the next scan position. This second scan position, as represented by steps 146 and 150, may be measured and adjusted using the same above-described, or a similar, method. Alternatively, it may be noted, the second scan position may be calculated mathematically based on the known location of the first scan position.

Next, at step 152, the program adjusts the gain and offset of the imaging board 74 in order to achieve the optimal image intensity and contrast. To complete this adjustment, the area of photographic scale 16 and opaque white region 20 is projected onto the pixel array to form an image. The gray values of the pixels in the image of each of the seven strips 16a–16g of the photographic scale 16 are measured. On the basis of these measured gray values, the electronic gain and offset of the imaging processing board 74 are gradually adjusted until the gray values for the pixels in the image of the photographic scale reach desired values or ranges.

For example, in an embodiment of the invention that has been actually reduced to practice, the four optical density levels are 2.5, 0.44, 0.19 and 0.09. Under preferred adjusted values, the intensity levels of the images corresponding to these four optical density values are 0, 82, 140 and 180, respectively. In the calibration of the imaging system, the gain and offset of the imaging board are adjusted so that the intensity levels are equal to, or very close to, the above-defined values.

These measured gray values for the pixels in the image of the photographic scale are primarily determined by the lamp located in the side of the calibration cassettes 10 that is opposite the pixel array 60. To check the condition of the lamp that is on the same side of the calibration cassette as the pixel array, the gray value for the pixels in the image of the opaque white region 20 is measured. If this gray value is within a desired range, the program signals to the operator that the lamp is in good condition; however, if that gray value is outside of the desired range, the program displays an error message and requests that the operator change the lamps.

After completing the gain and offset adjustment and the lamp verification, additional scan positions of the cassette may be adjusted, as represented by step 154. In particular, the calibration cassette 10 is moved to the third scan position at step 156, and this third scan position is adjusted at step 160 using a method that is the same as, or similar to, the method used to adjust the first two scan positions. Then, at step 162 the cassette 10 is turned 180° and the fourth scan position is adjusted, as represented by steps 164 and 166, again using the same, or similar, method used to adjust the first and second scan positions. The cassette is then turned 180° and moved back to the first scan position, as represented by steps 170 and 172. Measurements are not necessary to adjust the fifth and sixth scan positions of cassette 10 because the specific locations for these latter two scan positions can be calculated from the previously determined scan positions.

The determination of the precise scan positions completes the adjustment procedure; and once this is done, the results of the adjustments and the performance of the software for the agglutination analysis are checked. To do this, the program reads the reactions printed at 22a–22d on the calibration cassette and verifies the results. To perform this verification, the calibration cassette 10 is, at step 172, moved to the first scan position and an image of the first two reaction columns 22a and 22b is generated on the pixel array 60. The data values for the pixels in the image of each reaction column are processed, at step 174, by a predetermined image processing program, for example as described in copending patent application Ser. No. 08/163,996, for "Method and system for classifying Agglutination Reactions." In particular, by analyzing this image data, the image processing program extracts the features that are directly related to the agglutination reactions, such as (1) the size of the cell pellet; (2) the shape of the cell pellet border; (3) the location and size of red cell agglutinates in the column; and (4) the side to side balance of red cells in the column.

Once these feature values are obtained, a software program, referred to as a reaction classification program, transforms a set of feature values into one of a plurality of predefined reaction classes, such as positive, negative, indeterminate, or special type reaction. The positive reaction, may be further classified as +0.5, +1, +2, +3, or +4 reactions. The special reactions may also be further classified, or more specifically identified as, for example, hemolysis, a mixed field, or as reactions in which too many or too few cells were added.

After the verification of the first two reactions pictures 22a and 22b, the calibration cassette 10 is, at step 176, moved to the third scan position, and the image data from the two remaining reaction pictures 22c and 22d is generated. This reaction image data are, at step 180, processed and classified by the same image data processing program. The cassette 10 can be moved back to carousel 90, as represented by step 182. After finishing the analysis of all four reaction pictures, the program compares the obtained feature values and reaction classes of the four reactions to the predefined, known values.

If the extracted feature values from the reaction images 22a–22d of the calibration cassette are within required ranges and the reactions are correctly classified, the calibration procedure is completed and the program signals the operator that the instrument 30 is ready for use in real sample testing. If one or more feature values are out of the associated, desired range or a wrong classification is obtained, or both, then the operator may check for defects in the calibration cassette 10 or in the image processing system 30 and repeat the entire calibration procedure. If an error occurs again, the operator may be alerted not to use the analysis instrument 30 and to request service, maintenance or repair of the instrument.

It should be noted that the procedure described herein in detail is not the only method for performing the calibration. For example, the same objectives can be achieved even though the specific order of the calibration steps may be changed or different image processing methods may be used.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. An article of manufacture for calibrating a system for analyzing agglutination reactions, the article of manufacture comprising:

a base having at least first and second, transparent areas;

a plurality of reaction images on the first transparent area of the base, each of said reaction images showing results of an agglutination reaction; and a gray scale on the second transparent area of the base, the gray scale including a plurality of strips having different optical densities.

2. An article of manufacture according to claim 1, wherein the base includes a third, opaque area for reflecting light.

3. An article of manufacture according to claim 1, wherein the plurality of reaction images includes four reaction images showing results of four different agglutination reactions.

* * * * *